United States Patent
Gunzer et al.

(12) 
(10) Patent No.: US 6,306,617 B1
(45) Date of Patent: Oct. 23, 2001

(54) LIQUID REAGENT TO DETECT CREATINE KINASE

(75) Inventors: Gerhard Gunzer, Co. Clare (IE); Frank Kretzschmar, Dohna OT Borthen (DE); Katy Wrynn, Co. Clare (IE)

(73) Assignee: Olympus Diagnostica GmbH, Hamburg (DE)

( * ) Notice: Subject to any disclaimer, the term of this patent is extended or adjusted under 35 U.S.C. 154(b) by 0 days.

(21) Appl. No.: 09/468,416

(22) Filed: Dec. 20, 1999

(30) Foreign Application Priority Data

Dec. 22, 1998 (DE) ............................... 198 59 261

(51) Int. Cl.⁷ ............................... C12Q 1/50; C12N 9/00; C12N 9/12
(52) U.S. Cl. .............................. 435/17; 435/183; 435/194
(58) Field of Search ................ 435/17, 183, 194

(56) References Cited

U.S. PATENT DOCUMENTS 5,716,797 * 2/1998 Danno et al. ...................... 435/17

FOREIGN PATENT DOCUMENTS

| 31 38602 A1 | 12/1998 | (DE) . |
| 95/30769 | 5/1994 | (WO) . |

* cited by examiner

*Primary Examiner*—Louise N. Leary
(74) *Attorney, Agent, or Firm*—Rankin, Hill, Porter & Clark LLP

(57) ABSTRACT

A liquid reagent for detecting creatine kinase activity. The liquid reagent includes G6PDH, hexokinase, creatine phosphate, glucose, ADP, NAD(P) and thioglycerol, which are split into two separate batches of reagents for storage. G6PDH is contained in one batch, and thioglycerol together with a further substance is contained in the other batch. The batches of reagents are mixed together prior to use for detection purposes.

20 Claims, No Drawings

LIQUID REAGENT TO DETECT CREATINE KINASE

BACKGROUND OF THE INVENTION

The present invention relates to a liquid reagent for detecting creatine kinase.

Creatine kinase is used for bodily catalysis of the ATP-dependent phosphorylation of creatine into creatine phosphate (to-and-fro reaction). Creatine kinase is found in the body, for instance in the brain, in the heart muscle and the skeletal musculature. Increased creatine kinase values in the heart muscle are present at cardiac infarction, and in the skeletal musculature they indicate muscle pathologies (for instance muscular dystrophy). Renal insufficiency is accompanied for instance with a rise in creatine kinase activity in the serum.

Accordingly creatine kinase activity represents a routinely checked and significant clinical parameter.

A current detection system for creatine kinase activity operates according to the reaction below:

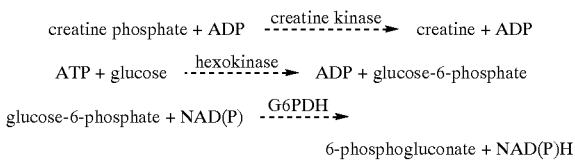

In this detection, creatine kinase activity is determined indirectly by means of the NAD(P)H content with absorption measurement at 340 nm.

Conventional liquid reagents used in detecting creatine kinase, for instance by means of the above reaction, contain the required substrates, co-substrates and enzymes and optionally and illustratively stabilizing or bactericidal substances etc. In many cases, the reagents required for the reactions of detection are split in such manner into two reaction batches so that no undesired enzymatic decomposition reactions take place during storage. The reagent batches are mixed to form the liquid reagent (test reagent) and the reactions of detection take place only thereafter in the test sample as a function of creatine kinase activity.

The above described detection procedure is relatively reliable and is used in many creatine kinase activity tests.

However, it does entail a problem in that creatine kinase is comparatively rapidly inactivated for instance in serum. For that reason, liquid reagents of this species contain a creatine kinase reactivator. A suitable reactivator is a component containing SH groups, typically N-acetylcysteine, (NAC hereafter), which is suitable for freeze drying.

However, NAC is rated only as a conditionally appropriate reactivator in the literature (Morin, Clinical chemistry, vol 23, #9, September 1977, pp 1569–1575). In particular it was found that the reactivator effect of NAC drops following a substantial length of storage because of formation of inhibitors, and as a result special substances to stabilize NAC are present in many detection systems containing NAC.

On this ground, the above cited publication recommends other reactivators, in particular thioglycerol to which is ascribed substantially increased reactivation performance and storage stability compared to NAC.

However, applicant has found that problems remain even when using thioglycerol in liquid reagents for detecting creatine kinase, in particular, as regards stability.

As a result, thioglycerol is predominantly used separately in the known liquid reagents. Illustratively, the German patent 31 38 602 discloses a liquid reagent of two reagent batches, one of which is essentially a thioglycerol buffer. In this batch, the thioglycerol is not meant to be a reactivator. Instead, before the analysis proper, a sample is added to the reagent batch containing thioglycerol to eliminate clouding. Thereupon the cleared sample is mixed with the second reagent batch which contains the actual detection reagents.

The patent document WO 95/30769 describes a liquid reagent of which one batch acts as the activator solution of which the main ingredient is thioglycerol. The other substances needed for detection are contained in the other reagent batches. The described liquid reagent offers improved thioglycerol stability. However, on account of the additional batch (almost always the known liquid reagent consists of a total of three batches) handling is made more difficult.

SUMMARY OF THE INVENTION

Therefore it is the objective of the invention to create a liquid reagent of the initially cited kind which contains thioglycerol as the reactivator, which is stable over a long time and allows detection with fair simplicity.

Accordingly, the invention provides a liquid reagent to detect creatine kinase activity and containing the following substances: glucose-6-phosphate dehydrogenase (hereafter G6PDG), hexokinase, creatine phosphate, glucose, ADO, NAD(P) and thioglycerol, these substances being split in such manner into two separate batches of reagents that thioglycerol and at least one further substance are contained in one batch, and G6PDH and any remaining substances are contained in the other batch, of reagents.

It was found that on account of the separation of the invention of G6DPH and thioglycerol, and where called for further conventionally used substances such as NADP, glucose, hexokinase, ADP, AMP or MG, the storage stability of both batches of reagents, and thereby that of the liquid reagent, can be substantially increased as a whole.

DETAILED DESCRIPTION OF THE PREFERRED EMBODIMENTS

Since the stability of at least a few of the substances contained in the liquid reagent depends on the pH value, a further implementation of the invention provides that the batches of reagents shall be of different pH values. When the substances are appropriately split into batches, storage stability can then be optimized.

One of the batches of reagents will then be adjusted to a weakly basic pH value in the range of 8.0 to 10.0 (measured at 20° C.), whereas the other batch of reagents will be adjusted to a weakly acid pH value between 5.5 and 7.0. Based on the above, another implementation of the invention provides that G6PDH and/or ADP are advantageously added to the weakly basic batch of reagents because these substances are more stable at higher pH values.

Preferably, the pH values and the quantitative ratios of the batches of reagents are selected in such a manner that after being mixed together, the resulting finished liquid reagent (test reagent) will have a pH value of about 6.0 to 7.0, in particular 6.5.

In this respect, a zwitter-ionic buffer is provided in especially advantageous manner in one of the batches of reagents, of which one pK value is situated at pH values between 8.0 and 10.0 and of which the other pK value is situated at pH values between about 5.5 and 7.0. During storage, this buffer adjusts the batch of reagents to a basic pH value and, following mixing with the other batch of reagents, changes to the desired detection pH of 6.0 to 7.0, in particular to 6.5. When using a zwitter-ionic buffer, for instance a bis-tris-propane buffer with pK values in the range of the above stated pH values, it is possible to reduce the buffer volume compared to the use of conventional buffers.

It was further found that the conventionally employed G6PDH undergoes undesired reactions in the presence of glucose and NAD(P). Therefore, another advantageous implementation of the invention provides that the said three substances shall not be jointly present in one batch of reagents.

Another problem relates to the thioglycerol stability. The proteins conventionally used to stabilize enzymes and SH compounds, for instance BSA or gelatin, in the case of thioglycerol rather cause a decrease in stability. Therefore, in lieu of proteins, sugar derivatives such as mannitol or polyethylene glycol 6000 or also long-chain alkyl compounds commercially known as Synperonic, are added, which preserve the stability of the auxiliary enzymes (hexokinase and G6PDH), and which are free of components that decompose thioglycerol.

It was also found that hexokinase is stabilized by the presence of glucose. Therefore, these two substances are preferably present in one batch of reagents.

The test reagent of the invention may contain further substances such as EDTA as an antioxidizer, $NaN_3$ and gentamicin sulfate as a bactericide or fungicide. Moreover, AMP and $AP_5A$ may be added which, in their role as competitive inhibitors of adenylate kinase, contribute to reducing the danger of spuriously positive signals. The test reagent may further contain magnesium acetate which together with ADP, forms a pre-complex and thereby increases the creatine kinase activity.

Lastly, as regards the batch that is free of thioglycerol, it may also contain a protein, for instance gelatin or BSA to stabilize G6PDH.

Finally, the invention is not limited to strictly employing thioglycerol. It is possible furthermore to use other reactivators, for instance the initially mentioned NAC.

In the invention, applicable detection reagents illustratively may be of the compositions shown in the Table below:

TABLE

| | Possible range of concentration | Preferred concentration in batch |
|---|---|---|
| Reagent batch 1 | | |
| imidazole buffer | 82 mmol/ltr | 50–150 mmol/ltr. |
| EDTA | 2.5 mmol/ltr | 2–3 mmol/ltr. |
| glucose | 25 mmol/ltr | 20–50 mmol/ltr. |
| magnesium acetate | 12.5 mmol/ltr | 10–15 mmol/ltr. |
| AMP | 6.5 mmol/ltr | 5–10 mmol/ltr. |
| $AP_5A$ | 0.013 mmol/ltr | 0.01–0.05 mmol/ltr. |
| NADP | 2.5 mmol/ltr | 2–5 mmol/ltr. |
| $NaN_3$ | 0.095% | |
| gentamicin sulfate | 0.005% | |
| PEG 6000 | 2.0% | 0.5–5% |
| mannitol | 1.0% | 1–5% |
| Synperonic | 0.1% | 0.05–0.2% |
| hexokinase | 7.5 kU/ltr. | 3–10 kU/ltr. |
| thioglycerol | 26 mmol/ltr. | 20–100 mmol/ltr. |
| NAC | 0.2 mmol/ltr. | 0–2.0 mmol/ltr. |

TABLE-continued

| | Possible range of concentration | Preferred concentration in batch |
|---|---|---|
| The pH value is set at 6.20 ± 0.20 at 20° C. | | |
| Reagent batch 2 | | |
| G6PDH | 20 kU/ltr. | 10–30 kU/ltr. |
| bis tris propane | 70 mmol/ltr | 50–100 mmol/ltr. |
| CP | 50 mmol/ltr | 30–70 mmol/ltr. |
| ADP | 5 mmol/ltr | 3–6 mmol/ltr. |
| $NaN_3$ | 0.095% | |
| gentamicin sulfate | 0.005% | |
| gelatin | 0.2% | 0.1–0.5% |
| mannitol | 1% | 1–5% |
| Synperonic | 0.1% | 0.05–0.2% |

The pH value was adjusted to 9.20±0.20 at 20° C.

The batches of reagents were mixed in the ratio of 4/1 (4 parts of batch 1, and 1 part of batch 2) to form the test reagent.

The above information relates to a preferred embodiment of the test reagent of the invention. It is understood that the invention also covers other compositions containing fewer or also other substances, for instance other buffers or stabilizing reagents.

What is claimed is:

1. A liquid reagent to detect creatine kinase activity, said liquid reagent comprising at least the following substances: G6PDH, hexokinase, creatine phosphate, glucose, ADP, NAD(P) and thioglycerol, the substances being split into two separate batches of reagents and the batches of reagents being mixed for detection purposes, wherein G6PDH is contained in one batch, and thioglycerol together with at least a further substance is contained in the other batch.

2. The liquid reagent of claim 1, wherein one of the batches of reagents is adjusted to a weakly acid pH value between 5.5 and 7.0 and the other batch is adjusted to a weakly basic pH value of 8.0 to 10.0.

3. The liquid reagent of claim 2, wherein the quantitative ratios and the pH values of the batches of reagents are selected such that following the mixing of the batches of reagents, the liquid reagent assumes a pH value in the range of 6.0 to 7.0.

4. The liquid reagent of claim 2, wherein a zwitter-ionic buffer is present in the basic batch of reagents and its pK value is situated at pH values between 8.0 and 10.0 and the other pK value is situated at pH values between 5.5 and 7.0.

5. The liquid reagent of claim 2, wherein G6PDH and ADP are present in the basic batch of reagents.

6. The liquid reagent of claim 1, wherein NAD(P), glucose and G6PDH are not jointly present in one batch of reagents.

7. The liquid reagent of claim 1, wherein glucose and hexokinase are present in one batch of reagents.

8. The liquid reagent of claim 3, wherein after the mixing of the batches of reagents, the liquid reagent assumes a pH value of about 6.5.

9. The liquid reagent of claim 3, wherein a zwitter-ionic buffer is present in the basic batch of reagents and its pK value is situated at pH values between 8.0 and 10.0 and the other pK value is situated at pH values between 5.5 and 7.0.

10. The liquid reagent of claim 3, wherein G6PDH and ADP are present in the basic batch of reagents.

11. The liquid reagent of claim 4, wherein G6PDH and ADP are present in the basic batch of reagents.

12. The liquid reagent of claim 2, wherein NAD(P), glucose and G6PDH are not jointly present in one batch of reagents.

13. The liquid reagent of claim 3, wherein NAD(P), glucose and G6PDH are not jointly present in one batch of reagents.

14. The liquid reagent of claim 4, wherein NAD(P), glucose and G6PDH are not jointly present in one batch of reagents.

15. The liquid reagent of claim 5, wherein NAD(P), glucose and G6PDH are not jointly present in one batch of reagents.

16. The liquid reagent of claim 2, wherein glucose and hexokinase are present in one batch of reagents.

17. The liquid reagent of claim 3, wherein glucose and hexokinase are present in one batch of reagents.

18. The liquid reagent of claim 4, wherein glucose and hexokinase are present in one batch of reagents.

19. The liquid reagent of claim 5, wherein glucose and hexokinase are present in one batch of reagents.

20. The liquid reagent of claim 5, wherein glucose and hexokinase are present in one batch of reagents.

* * * * *